United States Patent
Dubey et al.

(10) Patent No.: US 11,875,243 B2
(45) Date of Patent: Jan. 16, 2024

(54) INTELLIGENT AROMATIC SIMULATION OF FOOD RECIPE

(71) Applicant: Accenture Global Solutions Limited, Dublin (IE)

(72) Inventors: Alpana A. Dubey, Bangalore (IN); Veenu Arora, Sri Ganganagar (IN); Nitish A. Bhardwaj, Bangalore (IN); Aakanksha Saini, New Delhi (IN)

(73) Assignee: Accenture Global Solutions Limited, Dublin (IE)

( * ) Notice: Subject to any disclaimer, the term of this patent is extended or adjusted under 35 U.S.C. 154(b) by 93 days.

(21) Appl. No.: 17/572,800

(22) Filed: Jan. 11, 2022

(65) Prior Publication Data

US 2023/0222321 A1     Jul. 13, 2023

(51) Int. Cl.
| | | |
|---|---|---|
| *G06N 3/04* | (2023.01) | |
| *G06F 40/279* | (2020.01) | |
| *G06F 40/40* | (2020.01) | |
| *B05B 12/14* | (2006.01) | |
| *G06N 3/045* | (2023.01) | |
| *G06N 3/044* | (2023.01) | |

(52) U.S. Cl.
CPC ............. *G06N 3/045* (2023.01); *B05B 12/14* (2013.01); *G06F 40/279* (2020.01); *G06F 40/40* (2020.01); *G06N 3/044* (2023.01)

(58) Field of Classification Search
CPC ................................ G06N 3/045; G06N 3/044
See application file for complete search history.

(56) References Cited

U.S. PATENT DOCUMENTS

| | | | |
|---|---|---|---|
| 11,354,722 B1 * | 6/2022 | Singh | ................. G06Q 30/0633 |
| 2020/0084411 A1 | 3/2020 | Kim | |

OTHER PUBLICATIONS

Benjamin Sanchez, "Machine Learning for Scent: Learning Generalizable Perceptual Representations of Small Molecules", 2019 (Year: 2019).*
Wang Hao, "Learning Cross-Modal Embeddings with Adversarial Networks for Cooking Recipes and Food Images" (Year: 2019).*
Donghyeon Park, "KitcheNette: Predicting and Recommending Food Ingredient Pairings using Siamese Neural Networks" (Year: 2019).*
Chen ("Eating Healthier: Exploring nutrition information for healthier recipe recommendation") (Year: 2020).*
Extended Search Report in European Appln. No. 22186113.1, dated Jan. 4, 2023, 9 pages.

(Continued)

*Primary Examiner* — Ann J Lo
*Assistant Examiner* — Van C Mang
(74) *Attorney, Agent, or Firm* — Fish & Richardson P.C.

(57) ABSTRACT

Methods, systems, and computer-readable storage media for receiving, by an aromatic simulation platform, a recipe including descriptions indicative of ingredients of a consumable, processing the recipe through a first neural network to provide a recipe embedding, processing an ingredients profile to determine an aroma compounds profile representing the ingredients of the ingredients profile, processing the aroma compounds profile through a second neural network to provide an aroma embedding, and processing the recipe embedding and the aroma embedding through a third neural network to provide an aroma profile representative of the consumable of the recipe.

17 Claims, 5 Drawing Sheets

(56) References Cited

OTHER PUBLICATIONS

Nakamoto et al., "Cooking Up an Interactive Olfactory Game Display," IEEE Computer Graphics and Applications, Jan. 2008, 28(1):75-78.
AromaJoin.com [online], "Aroma Shooter®," available on or before Sep. 24, 2020 via Internet Archive: Wayback Machine URL<https://web.archive.org/web/20200924103415/https://aromajoin.com/products/aroma-shooter>, retrieved on Apr. 21, 2022, retrieved from URL<https://aromajoin.com/products/aroma-shooter>, 7 pages.
CIMAP.res.in [online], "AromaDb: A Database of Plant's Aroma Molecules," available on or before Sep. 2, 2018 via Internet Archive: Wayback Machine URL<https://web.archive.org/web/20180902112409/http://bioinfo.cimap.res.in/aromadb/>, retrieved on Apr. 21, 2022, retrieved from URL<https://web.archive.org/web/20220202145655/http://bioinfo.cimap.res.in/aromadb/>, 2 pages.
CoSyLab.iiitd.edu.in [online], "FlavorDB," available on or before Oct. 28, 2017 via Internet Archive: Wayback Machine URL<https://web.archive.org/web/20171028201429/https://cosylab.iiitd.edu.in/flavordb/>, retrieved on Apr. 21, 2022, retrieved from URL<https://cosylab.iiitd.edu.in/flavordb/>, 4 pages.
Food Flavors Chemical, Sensory and Technological Properties, 1st ed., Jelen (ed.), Oct. 25, 2011, 492 pages.
GitHub.com [online], "DGL-LifeSci," available on or before Sep. 9, 2020 via Internet Archive: Wayback Machine URL<https://web.archive.org/web/20200909193446/https://github.com/awslabs/dgl-lifesci>, retrieved on Apr. 21, 2022, retrieved from URL<https://github.com/awslabs/dgl-lifesci>, 4 pages.
GoogleBlog.com [online], "Learning to Smell: Using Deep Learning to Predict the Olfactory Properties of Molecules," Oct. 24, 2019, retrieved on Apr. 21, 2022, retrieved from URL<https://ai.googleblog.com/2019/10/learning-to-smell-using-deep-learning.html>, 5 pages.
Hanaoka, "Deep Neural Networks for Multicomponent Molecular Systems," ACS Omega, Aug. 10, 2020, 5(33):21042-21053.
Hu et al., "Strategies for Pre-training Graph Neural Networks," arXiv, Feb. 18, 2020, arXiv:1905.12265v3, 22 pages.
Marín et al., "Recipe1M+: A Dataset for Learning Cross-Modal Embeddings for Cooking Recipes and Food Images," IEEE Trans. Pattern Anal. Mach. Intelligence, Jul. 9, 2019, 43(1):187-203.
Matsukura et al., "Smelling screen: Presenting a virtual odor source on a LCD screen," Presented at Proceedings of IEEE Virtual Reality 2013, Lake Buena Vista, FL, USA, Mar. 18-20, 2013, 167-168.
MIT.edu [online], "Recipe1M+: A Dataset for Learning Cross-Modal Embeddings for Cooking Recipes and Food Images," available on or before Jul. 18, 2017 via Internet Archive: Wayback Machine URL<https://web.archive.org/web/20170718062203/http://im2recipe.csail.mit.edu/>, retrieved on Apr. 21, 2022, retrieved from URL<http://im2recipe.csail.mit.edu/>, 8 pages.
Ranasinghe et al., "Digital Lollipop: Studying Electrical Stimulation on the Human Tongue to Simulate Taste Sensations," ACM Trans. Multimedia Comput. Commun. Applications, Feb. 2017, 13(1):5, 22 pages.
Ranasinghe et al., "Vocktail: A Virtual Cocktail for Pairing Digital Taste, Smell, and Color Sensations," Presented at Proceedings of the 25th ACM International Conference on Multimedia, Mountain View, CA, USA, Oct. 23-27, 2017, 1139-1147.
Salvador et al., "Learning Cross-modal Embeddings for Cooking Recipes and Food Images," Presented at Proceedings of IEEE Conference on Computer Vision and Pattern Recognition (CVPR), Honolulu, HI, USA, Jul. 21-26, 2017, 3068-3076.
Sanchez-Lengeling et al., "Machine Learning for Scent: Learning Generalizable Perceptual Representations of Small Molecules," arXiv, Oct. 25, 2019, arXiv:1910.10685v2, 18 pages.
YouTube.com [online], "[MM2017] Vocktail: A Virtual Cocktail for Pairing Digital Taste, Smell, and Color Sensations," Oct. 19, 2017, retrieved on Apr. 21, 2022, retrieved from URL<https://www.youtube.com/watch?v=RQI6UDP1kOQ&ab_channel=NimeshaRanasinghe>, 4 pages [Video Submission].
YouTube.com [online], "Have a multisensory meal at Shanghai's best restaurant | One Cool Thing," Feb. 1, 2016, retrieved on Apr. 21, 2022, retrieved from URL<https://www.youtube.com/watch?v=D895BLjU13s&ab_channel=Insider>, 3 pages [Video Submission].

* cited by examiner

INTELLIGENT AROMATIC SIMULATION OF FOOD RECIPE

BACKGROUND

With recent development in sensory interfaces, consumables in the real world, such as food or drinks, can be experienced virtually. An example sensory interface includes an aroma diffuser that provides aroma and, to some extent, taste simulation of consumables. The sensory interfaces can be programmed to simulate different sensory experiences from different recipes of consumables. This enables expansion of sensory testing, customization, and social sharing experiences.

Recently, there has been research directed to enhancing virtual sensory experiences. However, existing virtual simulation toolkits and sensory interfaces are limited by their static nature. For example, existing simulations can only be used based on pre-defined recipes of consumables (e.g., food, drink). When there are changes to the recipe, such as changes to some of the ingredients or adjustments to the proportion of the ingredients, the output for creating the sensory experience cannot be efficiently adapted to those changes using existing technology.

SUMMARY

Implementations of the present disclosure are directed to an artificial-intelligence-enabled (AI-enabled) aromatic simulation platform for enriched aromatic experience of consumables, such as food (food recipes) and drink (drink recipes). More particularly, implementations of the present disclosure are directed to an AI-enabled aromatic simulation platform that leverages AI models to predict an aroma profile from a recipe of a consumable (e.g., food, drink). The aroma profile can be used by an aroma diffuser to generate an aroma representative of the recipe, which can create a virtual sensory experience of the consumable.

In some implementations, actions include receiving, by an aromatic simulation platform, a recipe including descriptions indicative of ingredients of a consumable, processing the recipe through a first neural network to provide a recipe embedding, processing an ingredients profile to determine an aroma compounds profile representing the ingredients of the ingredients profile, processing the aroma compounds profile through a second neural network to provide an aroma embedding, and processing the recipe embedding and the aroma embedding through a third neural network to provide an aroma profile representative of the consumable of the recipe. Other implementations of this aspect include corresponding systems, apparatus, and computer programs, configured to perform the actions of the methods, encoded on computer storage devices.

These and other implementations can each optionally include one or more of the following features: actions further include processing, by an aroma diffuser, the aroma profile to determine a quantity to release from each aroma cartridge in a set of aroma cartridges, each aroma cartridge corresponding to a scent, and releasing, by the aroma diffuser, a mix of scents from the set of aroma cartridges based on respective quantities; the scent corresponds to part of the aroma compounds, and the aroma profile is indicative of proportion of each scent in the mix of scents; the recipe is a new recipe or a modified recipe with changes in comparison with one of the recipes stored in a database; actions further include extracting, by the first neural network, ingredient vocabularies from descriptions representative of the ingredients in the recipe, encoding, by the first neural network, the ingredient vocabularies to provide an ingredient embedding, extracting, by the first neural network, instruction vocabularies from descriptions representative of instructions in the recipe, encoding, by the first neural network, the instruction vocabularies to provide an instruction embedding, and combing the ingredient embedding and the instruction embedding to provide the recipe embedding; actions further include deriving, by the second neural network, molecular embedding vectors corresponding to each aroma compound, extracting, by the second neural network, quantities of each of the aroma compounds from the recipe to derive weights of each aroma compound, processing, by the second neural network, to mix the molecular embedding vectors and the weight corresponding to the same aroma compound to derive a set of weight-mixed molecular embedding vectors, and deriving, by the second neural network, the aroma embedding based on the weight-mixed molecular embedding vectors; and the third neural network includes a bi-directional long short-term memory (BiLSTM) model.

The present disclosure also provides a computer-readable storage medium coupled to one or more processors and having instructions stored thereon which, when executed by the one or more processors, cause the one or more processors to perform operations in accordance with implementations of the methods provided herein.

The present disclosure further provides a system for implementing the methods provided herein. The system includes one or more processors, and a computer-readable storage medium coupled to the one or more processors having instructions stored thereon which, when executed by the one or more processors, cause the one or more processors to perform operations in accordance with implementations of the methods provided herein.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

DESCRIPTION OF DRAWINGS

Like reference symbols in the various drawings indicate like elements.

DETAILED DESCRIPTION

Figure 1:
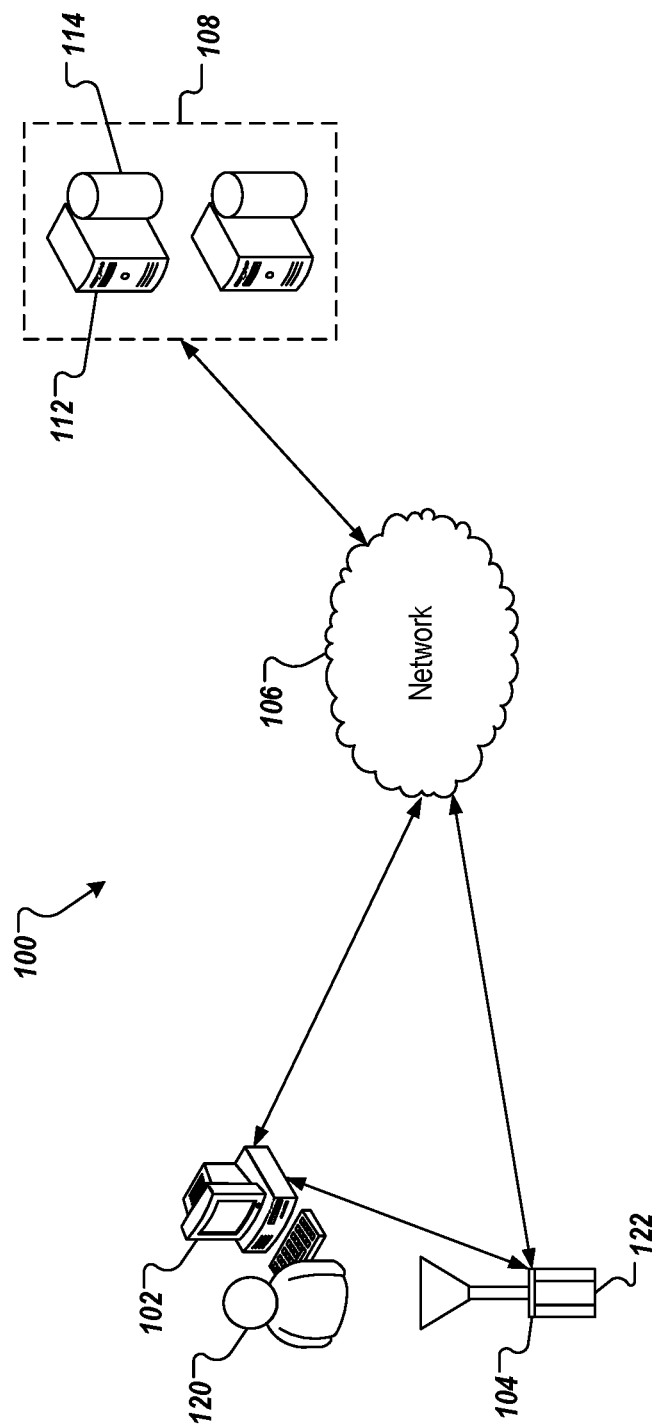
FIG. 1 depicts an example architecture in accordance with implementations of the present disclosure.

Implementations of the present disclosure are directed to an artificial-intelligence-enabled (AI-enabled) aromatic simulation platform for enriched aromatic experience of consumables, such as food (food recipes) and drink (drink recipes). More particularly, implementations of the present disclosure are directed to an AI-enabled aromatic simulation platform that leverages AI models to predict an aroma profile from a recipe of a consumable (e.g., food, drink). The aroma profile is used by an aroma diffuser to generate an aroma representative of the recipe to create a virtual sensory experience of the consumable.

Implementations can include actions of receiving, by an aromatic simulation platform, a recipe including descriptions indicative of ingredients of a consumable, processing the recipe through a first neural network to provide a recipe embedding, processing an ingredients profile to determine an aroma compounds profile representing the ingredients of the ingredients profile, processing the aroma compounds profile through a second neural network to provide an aroma embedding, and processing the recipe embedding and the aroma embedding through a third neural network to provide an aroma profile representative of the consumable of the recipe.

Implementations of the present disclosure are described in further detail herein with reference to example consumables (e.g., food, drink), example recipes, and example aroma profiles. It is contemplated, however, that implementations of the present disclosure can be realized with any appropriate consumable, recipe, and/or aroma profile.

To provide further context for implementations of the present disclosure, and as introduced above, with developments in sensory interfaces, consumables in the real world, such as food or drinks, can be experienced virtually. An example sensory interface includes an aroma diffuser that provides aroma and, to some extent, taste simulation of consumables. The sensory interfaces can be programmed to simulate different sensory experiences from different recipes of consumables. This enables expansion of sensory testing, customization, and social sharing experiences. However, existing virtual simulation toolkits and sensory interfaces are limited by their static nature. For example, existing simulations can only be used based on pre-defined recipes of consumables (e.g., food, drink). When there are changes to the recipe, such as changes to some of the ingredients or adjustments to the proportion of the ingredients, the output for creating the sensory experience cannot be efficiently adapted to those changes using existing technology.

In further detail, a recipe can include a set of ingredients, and an amount of each ingredient, and a set of instructions for preparing a consumable using the set of ingredients. An example recipe for a coffee tonic can be considered and is provided as:

| Listing 1: Example Recipe | |
|---|---|
| Name: | Mint, Basil and Tropical Fruit Coffee Tonic |
| Description: | This tropical fruit coffee is flavored with fresh mint and basil, making it an aromatic and flavorful. |
| Ingredients: | |
| | 25 ml - Coffee extract |
| | 100 ml - Grapefruit Syrup |
| | ½ cup - Mint, loosely packed |
| | ½ cup - Basil, loosely packed |
| Steps: | |
| | Add all ingredients into a high-powered blender, mix until well blended. |
| | Add milk if needed to help loosen the mixture. |
| | Serve immediately. |

In the example above, the recipe includes a name, a description, a set of ingredients, and a set of instructions for making the consumable from the set of ingredients.

To provide an aromatic sensory experience from a recipe, an aroma diffuser can be programmed with an aroma profile that models an aroma associated with a consumable represented by the recipe. An example aroma diffuser includes, without limitation, AromaShooter provided by Aromajoin Corporation. The aroma profile provides amounts of respective scents to be released from the aroma diffuser. For example, the aroma diffuser includes a set of cartridges, each cartridge holding a respective scent that corresponds to one or more ingredients. In some examples, a scent of each cartridge is provided from naturally extracted or artificially synthesized fluids that are atomized when released from the aroma diffuser. In some examples, the fluid within each scent includes aromatic compounds. For example, a scent "tropical grapefruit" can include aromatic compounds of Limonene, Beta-myrcene, Alpha-pinene, Sabinene, and Nootkatone.

In traditional approaches, recipes are individually processed by human experts to create respective aroma profiles representative of consumables (e.g., through manual testing, comparing, and evaluating procedures). An example aroma profile that can be provided based on the example recipe of Listing 1, above, can be provided as:

| Listing 2: Example Aroma Profile Aroma (on a scale of 0-10): | |
|---|---|
| Coffee: | 7 |
| Garden Spearmint: | 8 |
| Tropical Grapefruit: | 9 |
| Caramel: | 0 |
| Cinnamon: | 0 |
| Hazelnut: | 0 |
| Basil: | 8 |
| Fig Jam: | 0 |
| Black Pepper: | 0 |
| Blueberry: | 0 |
| Almond: | 0 |

As shown above, the aroma profile includes a set of scents and a relative amount of each scent. Each scent corresponds to a cartridge that can be used with the aroma diffuser. In general, scents can be representative of flavors, and the relative amount of each scent is representative of an intensity of each flavor relative to other flavors. For example, in the example of Listing 2, above, the scent of tropical grapefruit has the highest intensity, the scents of garden spearmint and basil have the next highest intensity, and the scent of coffee has the lowest intensity. Other scents that are present in the aroma diffuser (e.g., caramel, cinnamon, hazelnut, etc.) are not used (i.e., no intensity).

In some examples, the aroma profile can be sent to the aroma diffuser, which processes the aroma profile to release the scents in a manner that mixes the scents to simulate an aroma (smell) of the consumable of the recipe. That is, the aroma diffuser releases a mixture of scents from the set of cartridges based on the set of scents and respective intensities of each, as provided in the aroma profile. For example, in response to the example aroma profile of Listing 2, the aroma diffuser can release a mixture of scents with an amount of coffee scent corresponding to 7, an amount of garden spearmint corresponding to 8, an amount of tropical grapefruit corresponding to 9, and an amount of basil corresponding to 8.

However, in traditional approaches, the provision of aroma profiles from recipes is a bottleneck in time- and resource-efficiently providing sensory experiences. For example, each aroma profile is dependent on the effort of a human expert and is limited to the particularities of individual human experts. Consequently, aroma profiles for the same recipe can differ resulting in inconsistencies as between different human experts. As another example, changes to recipes cannot be time- and/or resource-efficiently represented in aroma profiles. For example, a recipe can be virtually experienced using a respective aroma profile. After virtually experiencing the recipe, one or more changes to the recipe could be desired (e.g., addition/removal of ingredient(s), adjusting amount of ingredient(s), modifying instructions for preparing the consumable). In response to the change(s), the human expert is needed to re-develop the aroma profile to reflect the changes. That is, the human expert needs to create a new aroma profile reflecting the changes. This is inefficient in terms of time and resources expended to react to such changes. For example, a virtual experience has to be put on hold (e.g., for days, weeks) until un updated aroma profile is provided.

Further, the number of aroma cartridges of an aroma diffuser can be limited (e.g., 6 cartridges in the AromaShooter). Consequently, recipes having pre-defined aroma profiles may not be able to be experienced using an aroma diffuser, if the aroma diffuser is incapable of holding all of the cartridges needed. For example, a pre-defined aroma profile that requires a number of different scents exceeding the number of cartridge slots available in the aroma diffuser cannot be (fully) experienced using the aroma diffuser (e.g., some scents of the aroma profile will be absent). In some instances, the pre-defined aroma profile can be adjusted to, for example, reduce the number of scents. Again, this is inefficient in terms of time and resources expended to make such changes.

In view of the above context, implementations of the present disclosure provide an AI-enabled aromatic simulation platform that leverages a set of AI models to generate an aroma profile from a consumable recipe. As described in further detail herein, the aromatic simulation platform processes a consumable recipe through the set of AI models to generate an aroma profile that is representative of an aroma of the consumable recipe. That is, the aroma profile is representative of an expected aroma of the consumable, if the consumable were to be created from the consumable recipe. In some implementations, the aroma profile can be sent to an aroma diffuser, which processes the aroma profile to release an aroma representative of the recipe to create a virtual sensory experience of the consumable. In some implementations, aroma compounds of ingredients represented in the consumable recipe are also analyzed and considered by the platform when generating the aroma profile.

FIG. 1 depicts an example system 100 that can execute implementations of the present disclosure. The example system 100 includes a computing device 102, an aroma diffuser 104, a network 106, and a back-end system 108. In some examples, the network 106 includes a local area network (LAN), wide area network (WAN), the Internet, or a combination thereof, and connects web sites, devices and back-end systems (e.g., the computing device 102, the aroma diffuser 104, the back-end system 108). In some examples, the network 106 can be accessed over a wired and/or a wireless communications link. For example, mobile computing devices, such as smartphones can utilize a cellular network to access the network 106.

In the depicted example, the back-end system 108 includes at least one server system 112 and data store 114 (e.g., database). In some examples, the at least one server system 112 hosts one or more computer-implemented services that users can interact with using computing devices. For example, the server system 112 can host one or more components of the aromatic simulation platform of the present disclosure. In some implementations, the aromatic simulation platform includes a set of AI models. Example AI models include neural networks that can include, without limitation, deep neural networks (DNNs) and graph neural networks (GNNs). As described in further detail herein, a consumable recipe is processed through the set of AI models to provide an aroma profile representative of an (expected) aroma of a consumable of the consumable recipe.

In some examples, the computing device 102 can include any appropriate type of computing device such as a desktop computer, a laptop computer, a handheld computer, a tablet computer, a personal digital assistant (PDA), a cellular telephone, a network appliance, a camera, a smart phone, an enhanced general packet radio service (EGPRS) mobile phone, a media player, a navigation device, an email device, a game console, or an appropriate combination of any two or more of these devices or other data processing devices. In the context of the present disclosure, a user 120 can use the computing device 102 to interact with the aromatic simulation platform. For example, the user 120 can input a consumable recipe (e.g., provided in a computer-readable file) that is processed by the aromatic simulation platform to provide an aromatic profile, as described in detail herein.

Also, in the context of the present disclosure, the user 120 (and/or other users) can use the aroma diffuser 104 for a virtual aromatic sensory experience of the consumable recipe. For example, the aroma diffuser 104 can receive an aroma profile (e.g., provided as a computer-readable file), which processes the aroma profile (e.g., through one or more computer-executable programs executed by one or more processing devices of the aroma diffuser 104) to release scents in a manner that mixes the scents to simulate an aroma (smell) of the consumable of the consumable recipe. That is, the aroma diffuser 104 releases a mixture of scents from a set of cartridges 122 based on a set of scents and respective intensities of each, as provided in the aroma profile.

In some implementations, consumable recipes and/or aroma profiles of respective consumable recipes (e.g., food recipes, drink recipes) can be stored in the database 114 of the server system 108. In some examples, chemical composition of aromatic compounds in each ingredient of the consumable recipes can be stored in the database 114 of the server system 108.

In some implementations, the aroma diffuser 104 communicates with the computing device 102 and/or the server system 108 through the network 106. In some examples, the aroma diffuser 104 is directly connected with the computing device 102 for communication (e.g., over a wired or a wireless connection). In some examples, the user 120 can use the computing device 102 to select a consumable recipe for aromatic simulation by the aroma diffuser 104. In response, the aromatic simulation platform (e.g., components thereof executing within the sever system 108) can generate an aroma profile, which can be transmitted to the aroma diffuser 104. In response to receiving the aroma profile, the aroma diffuser 104 can be operated to release a scent mixture based on the aroma profile, the scent mixture simulating a scent of a consumable of the consumable recipe, if the consumable were to actually be made.

Figure 2:
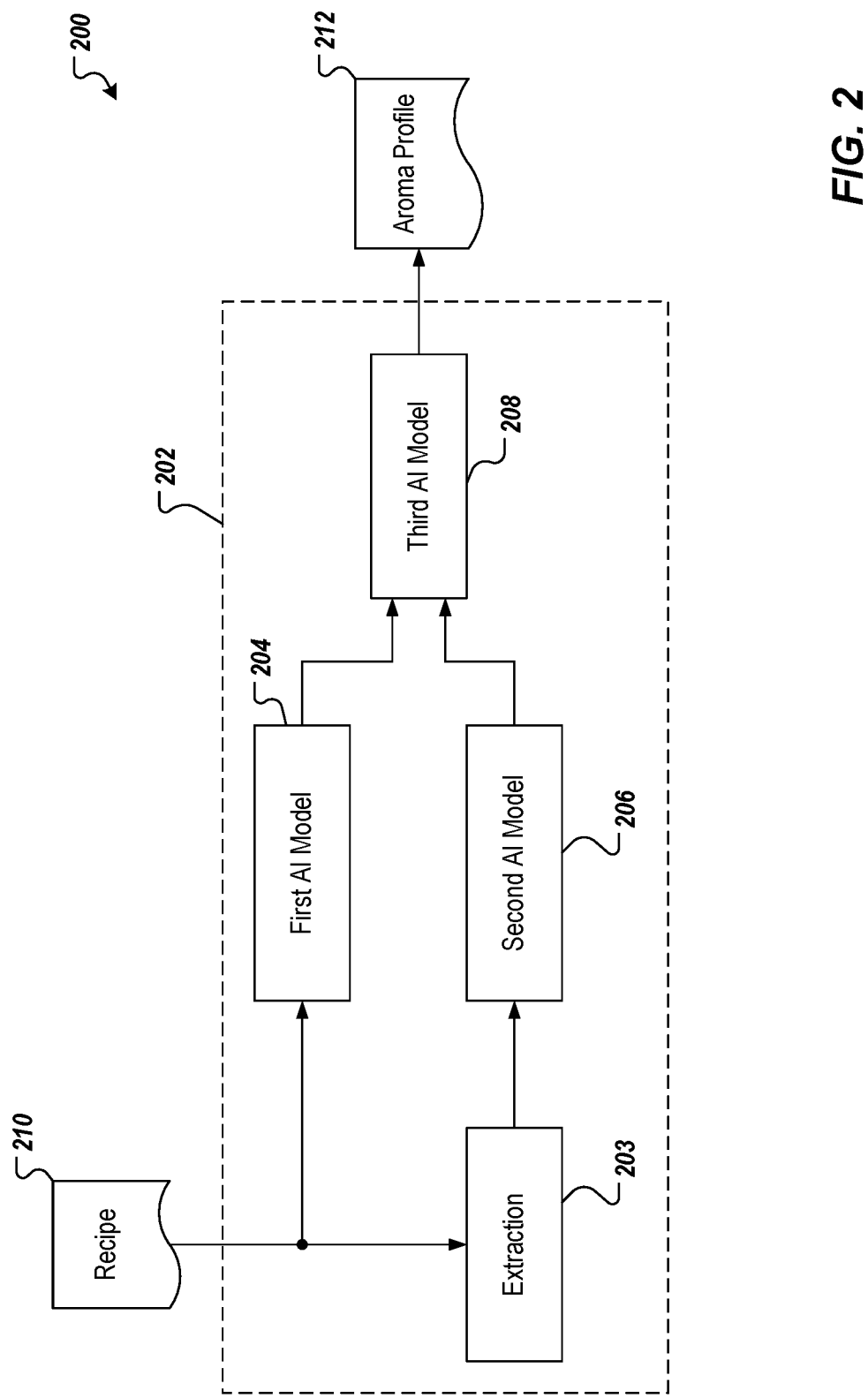
FIG. 2 depicts an example conceptual architecture of the aromatic simulation platform in accordance with implementations of the present disclosure.

FIG. 2 depicts an example conceptual architecture 200 including an aromatic simulation platform 202 in accordance with implementations of the present disclosure. In some examples, one or more components of the aromatic simulation platform 202 can be executed by a server system (e.g., the server system 108 of FIG. 1). In the example of FIG. 2, the aromatic simulation platform 202 includes an extraction module 203, a first AI model 204, a second AI model 206, and a third AI model 208.

As described in further detail herein, a consumable recipe 210 is received by the aromatic simulation platform 200. For example, the recipe 210 can be provided as a computer-readable file that is associated with a request sent from a computing device (e.g., the computing device 102, the aroma diffuser 104 of FIG. 1). The recipe 210 can include a description of the consumable, a set of ingredients, and a set of instructions for making the consumable from the set of ingredients.

In some implementations, the first AI model 204 receives the recipe 210 and processes the recipe 210 to provide a recipe embedding. The recipe embedding can be provided as a multi-dimensional numerical vector (e.g., n dimensions) that is representative of the recipe 210. In some examples, the first AI model 204 is provided as a DNN that is trained to extract information from the recipe 210 and transform the information into vector form, as the recipe embedding.

In some implementations, the extraction module 203 receives the recipe 210 and processes the recipe 210 to provide an ingredients profile. In some examples, the ingredients profile includes a set of ingredients identified in the recipe 210. In some examples, the extraction module 203 extracts ingredients identified in the recipe 210 based on information stored in an ingredients database (e.g., a library of ingredients that can be used in making consumables). In some examples, an amount of each ingredient in the set of ingredients is determined by the extraction module 203 and is recorded with the respective ingredients in the ingredients profile. The extraction module 203 can process the ingredients profile to determine an aroma compounds profile for each ingredient of the ingredients profile.

In some implementations, the extraction module 203 can determine a set of aroma compounds for each ingredient in the ingredients profile. For example, the extraction module 203 can transmit a request to a service, the request including the list of ingredients. In some examples, the service maintains a database of ingredients and, for each ingredient, a set of aroma compounds representative of a scent of the respective ingredient. For example, the service can maintain or otherwise access an aroma compounds database. An example aroma database includes, without limitation, AromaDB provided by the Council of Scientific and Industrial Research (CSIR) and the Central Institute of Medicinal and Aromatic Plants (CIMAP) of India. In some examples, in response to the request, the service returns, for each ingredient, a set of aroma compounds. In some examples, the set of aroma compounds includes, for each compound, a concentration. The extraction module 203 provides the aroma compounds profile as the list of ingredients, for each ingredient a set of aroma compounds, and, for each aroma compound, a concentration.

In some implementations, the second AI 206 receives the aroma compounds profile from the extraction module 203 and processes the aroma compounds profile to provide an aroma embedding. The aroma embedding can be provided as a multi-dimensional numerical vector (e.g., m dimensions) that is representative of an aroma of the recipe 210. In some examples, the second AI model 206 is provided as a GNN that is trained to extract information from the aroma compounds profile and transform the information into vector form, as the aroma embedding.

In some implementations, the recipe embedding and the aroma embedding are provided as parallel inputs to the third AI model 208.

In some implementations, the third AI model 208 receives the recipe embedding and the aroma embedding and processes both to provide an aroma profile 212 that is representative of an aroma of the consumable of the consumable recipe 210. In some examples, the aroma profile provided by the third AI model 208 can be described as representing a predicted aroma. In some examples, the third AI model 208 is provided as a classifier that is trained to classify a recipe with respect to a set of class labels, each class label representing a scent, each scent being assigned a value indicating an amount of the respective scent.

In some implementations, the first AI model 204, the second AI model 206, and the third AI model 206 of the aromatic simulation platform 202 are trained during a training phase. In some examples, training data includes a set of consumable recipes and, for each consumable recipe, an aroma profile. In some examples, each aroma profile includes scents of a set of scents. In this manner, the aroma profiles are each bounded to the set of scents and are absent scents that are not included in the set of scents. That is, the aroma profiles 212 provided by the aromatic simulation platform 202 only include scents that are available for the aroma diffuser (e.g., the aroma diffuser 104 of FIG. 1). In some examples, the set of scents includes scents that are available for release from an aroma diffuser (e.g., the aroma diffuser 104 of FIG. 1). For example, the aroma diffuser can have a limited set of scents available. In some examples, the aroma profiles used in training are limited in a number of scents. For example, the aroma profiles can be limited to a number of scents that is equal to a number of cartridge slots available in an aroma diffuser (e.g., the aroma diffuser 104 of FIG. 1). In this manner, aroma profiles 212 provided by the aromatic simulation platform 202 include a number of scents that is achievable by the aroma diffuser.

In some examples, an aroma compounds profile of each of scent in the set of scents can be considered during training of the aromatic simulation platform 200. For example, and as described in detail herein, a scent provided from an aroma cartridge can include an aroma compounds profile. The aroma compounds profile can include a list of aroma compounds that make up the scent and respective concentrations of the aroma compounds. An example scent can include, without limitation, spearmint, and the aroma compounds profile can be provided as:

TABLE 1

A example of aroma compounds profile of Spearmint

| Scent | Aromatic Compounds | Concentration (%) |
|---|---|---|
| Spearmint | carvone | 60.9-71.6 |
| | limonene | 11.4-21.2 |
| | dihydrocarvone | 1-4.9 |
| | 3-octanal | 1.3-2.6 |
| | menthone | 0.4-1.7 |
| | 1,8-cineol | 0.8-1.5 |

In general, the aromatic simulation platform 202 is iteratively trained, where, during an iteration, one or more parameters of the AI models 204, 206, 208 are adjusted, and an output is generated based on the training data (e.g., aroma profile prediction). For each iteration, a loss value is determined based on a loss function. The loss value represents a degree of accuracy of the output of the aromatic simulation platform 202. The loss value can be described as a representation of a degree of difference between the output of the aromatic simulation platform 202 and an expected output of the aromatic simulation platform 202 (the expected output being provided from training data). In some examples, if the loss value does not meet an expected value (e.g., is not equal to zero), parameters of the AI models 204, 206, 208 are adjusted in another iteration of training. In some instances, this process is repeated until the loss value meets the expected value.

Figure 3:
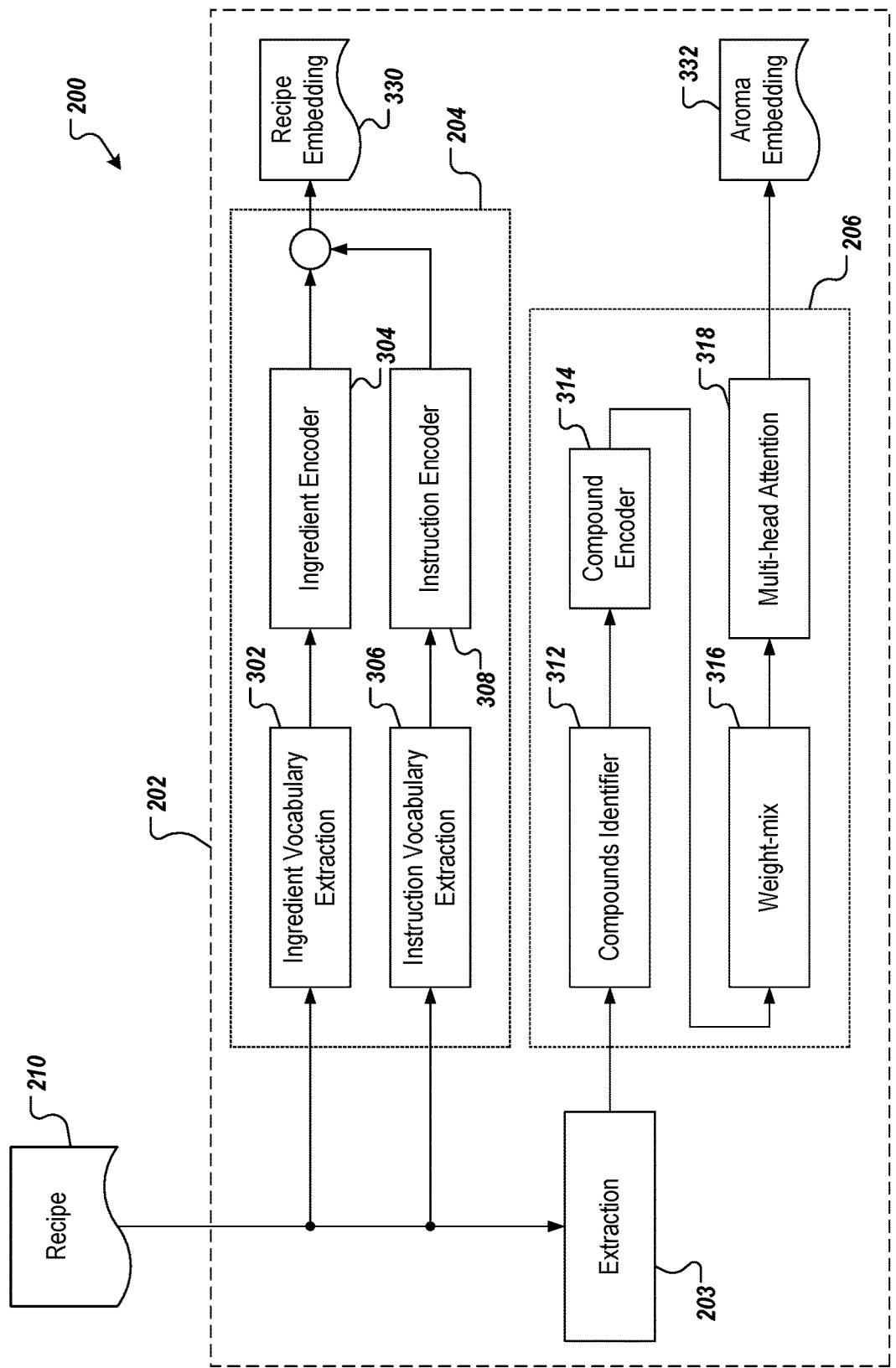
FIG. 3 depicts further detail of the example conceptual architecture of FIG. 2.

FIG. 3 depicts further detail of the example conceptual architecture 200 of FIG. 2. In the example of FIG. 3, the first AI model 204 of the aromatic simulation platform 202 includes an ingredient vocabulary extraction module 302, an ingredient encoder 304, an instruction vocabulary extraction module 306, and an instruction encoder 308. In the example of FIG. 3, the second AI model 206 of the aromatic simulation platform 202 includes a compounds identifier module 312, a compound encoder 314, a weight-mix module 316, and a multi-based attention network 318.

As described in further detail herein, the recipe 210 is processed by the first AI model 204 to provide a recipe embedding 330 and is processed by the extraction module 203 to provide an aroma compounds profile that is processed by the second AI model 206 to provide an aroma embedding 332. As introduced above, the recipe 210 can be provided as a computer-readable file and can include textual mark-up. For purposes of non-limiting illustration an example recipe and contents of a respective computer-readable file can be provided as:

Listing 3: Example Recipe
Strawberry Rhubarb Dump Cake

Ingredients
{'text': '6-8 cups fresh rhubarb, or'}
{'text': '6-8 cups frozen rhubarb, thawed'}
{'text': '1 12 cups granulated sugar'}
{'text': '6 ounces strawberry JellO gelatin dessert'}
{'text': '1 white cake mix (2 layer size)'}
{'text': '1 12 cups water'}
{'text': '12 cup butter or 12 cup margarine, melted'}
Instructions
{'text': 'Put ingredients in a buttered 9 × 12 × 2-inch pan in even layers in the order that they are given -DO NOT MIX.'}
{'text': 'Bake in a 350 oven for 1 hour.'}

The example of Listing 3 is provided from the Recipe1M dataset, which can be described as a large-scale, structured corpus of over one million cooking recipes that can be used for learning cross-modal embeddings for cooking recipes (see, e.g., Id: 00007bfd16, Partition: train, http://www.food.com/recipe/strawberry-rhubarb-dump-cake-408694). In some examples, the Recipe1M dataset is used in training of the aromatic simulation platform 202, as described above. As depicted in Listing 3, and as discussed in detail above, the recipe includes a name, a set of ingredients, and a set of instructions for making a strawberry rhubarb dump cake (consumable) from the set of ingredients.

In the example of FIG. 3, the ingredient vocabulary extraction module 302 of the first AI model 204 extracts the set of ingredients identified in the recipe 210 (e.g., fresh rhubarb, frozen rhubarb, granulated sugar, strawberry gelatin, white cake mix, water, butter, margarine). In some examples, quantities or proportions of the ingredients are also extracted from the recipe 210. In some implementations, the ingredient encoder 304 processes the set of ingredients and encodes the ingredients into an ingredient embedding. The ingredient embedding is provided as a multi-dimensional vector representation of the ingredients (e.g., p dimensions).

In the example of FIG. 3, the instructions vocabulary extraction module 306 of the first AI model 204 extracts the set of instructions identified in the recipe 210 (e.g., bake, 350°, 1 hour, do not mix). In some implementations, the instruction encoder 308 processes the set of instructions and encodes the instructions into an instruction embedding. The instruction embedding is provided as a multi-dimensional vector representation of the ingredients (e.g., q dimensions). In some implementations, the first AI model 204 combines the ingredient embedding and the instruction embedding to provide the recipe embedding 330. In some examples, the ingredient embedding and the instruction embedding are combined by concatenating the ingredient embedding and the instruction embedding to provide a combined embedding of high dimension (e.g., p+q dimensions).

Continuing with the example of FIG. 3, the extraction module 203 provides an aroma compounds profile. For example, and as described above, the extraction module 203 can transmit a request to a service, the request including the list of ingredients. In some examples, the service maintains a database of ingredients and, for each ingredient, a set of aroma compounds representative of a scent of the respective ingredient. In some examples, in response to the request, the service returns, for each ingredient, a set of aroma compounds. In some examples, the set of aroma compounds includes, for each compound, a concentration. The extraction module 203 provides the aroma compounds profile, which includes a set of aroma compounds, and, for each aroma compound, a concentration (e.g., as depicted in the example of Table 1).

The aroma compounds profile is processed by an identifier module 312, which transforms each aroma compound in the aroma compounds profile into identification (ID) information. In some examples, compounds (and/or molecules within compounds) can be mapped to an identifier that is based on a standard. An example standard includes, without limitation, the SMILES language for chemistry. Accordingly, for each aroma compound in the aroma compounds profile, the compounds identifier provides an identifier (e.g., SMILES identifier) to provide a set of identifiers (e.g., an identifier for each aroma compound in the aroma compound profile). The compound encoder 314 provides a compound embedding based on the set of identifiers. The compound embedding is provided as a multi-dimensional vector representation of the compounds. As a result, the compound embedding vectors can be seen as the vector representations of the aroma compounds of the recipe.

Each recipe is made of multiple ingredients which in turn are made up of multiple aromatic compounds. An ingredient's aroma is determined by the major aromatic compounds present in that ingredient. In order to capture an ingredient's aroma, the compound embedding vector from the compound encoder 312 for each compound in the aroma profile of the ingredient. In some examples, a relative importance of each compound towards the aroma of the ingredient is captured by using a ratio approach. For example, if a compound's concentration is 12% out of the total, a ratio of 12 to sum of concentrations of all major compounds is taken to represent its contribution to the aroma of the ingredient. The compound embedding vector for each aromatic compound is given as input to the weight mix model 316 of the second AI model 206, which combines the compound embedding vector from the compound encoder 312 and the weight (concentration ratio) corresponding to the same aromatic compound to derive a set of weight-mixed embedding vectors for each ingredient. These vectors in essence capture the aroma of each ingredient present in the recipe. In some examples, the weight-mixed embedding vectors can be processed by the multi-headed self-attention network 318 to provide the aroma embedding 332. In this manner, the aroma profile 212, that is ultimately predicted, is accurate to the recipe 210. Therefore, the aroma profile 212 not only accounts for the aromatic compounds, but also the concentrations of each.

Figure 4:
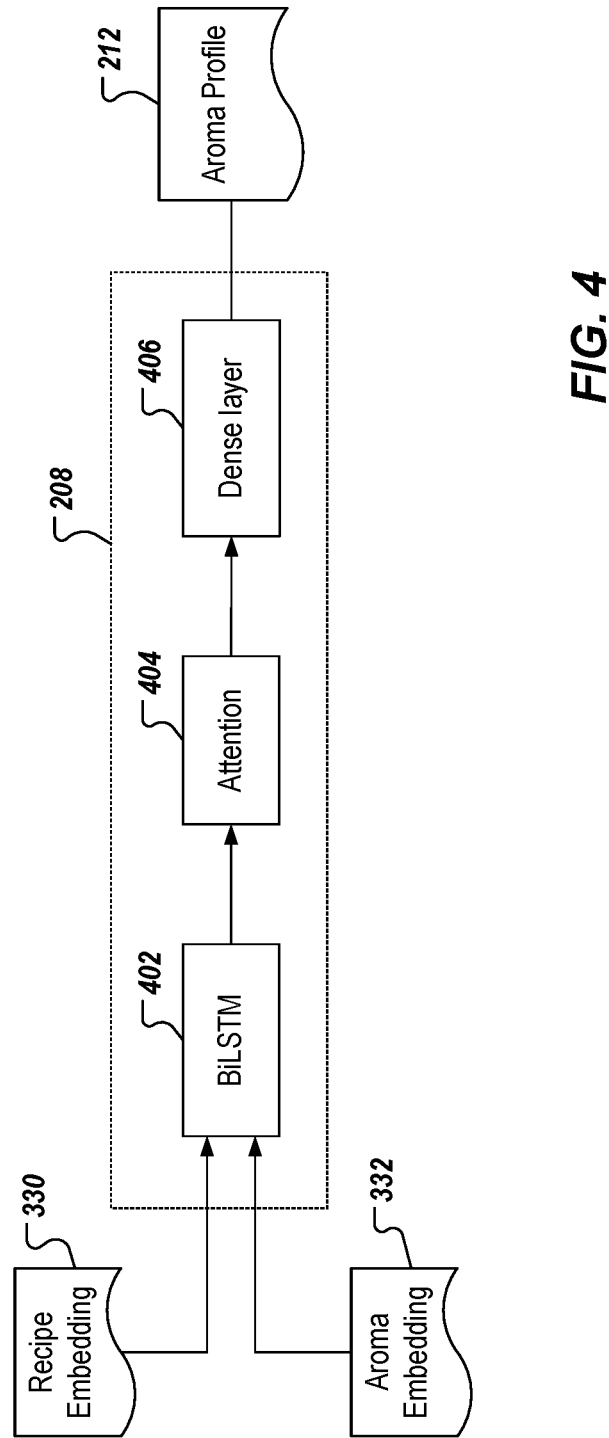
FIG. 4 depicts an example conceptual architecture of a neural network of the aromatic simulation platform in accordance with implementations of the present disclosure.

FIG. 4 depicts an example conceptual architecture of the third AI model 208 of FIG. 2. In the example of FIG. 4, the third ML model 208 includes a bi-directional long short-term memory (BiLSTM) module 402, an attention module 404, and a dense layer 406. In some implementations, the third ML model 208 receives the recipe embedding 330 and aroma embedding 332, respectively form the first AI model 204 and the second AI model 206. In some implementations the BiLSTM module 402 receives the recipe embedding 330 and aroma embedding 332 and processes each to derive an initial prediction result of an aroma profile. In some examples, a BiLSTM model in the BiLSTM module 402 can be replaced by other suitable neural network model to construct the relationship between recipe embedding, aroma embedding, and the prediction of aroma profile. In some examples, the initial prediction result of the aroma profile is processed by the attention module 404, and the dense layer 406, such that significant features in the initial prediction result can be optimized and the overall accuracy of the prediction can be improved.

In some examples, the prediction of aroma profiles of different recipes can be stored and analyzed (e.g., by the server system 104 of FIG. 1). For example, common scents among all of the aroma profiles can be identified. In this manner, cartridges can be procured to account for common scents and/or every scent identified in the aroma profiles.

In some examples, the aroma profiles can be analyzed and categorized based on similarity such that consumables with similar scents can be placed in the same category/class and tagged with same label. The labels and classes can be used for recommendation to users. In some examples, the prediction of aroma profiles and user feedback to the simulated sensory experience (e.g., through the mix of scents released from the aroma diffuser) can also be used for training the aromatic simulation platform.

Figure 5:
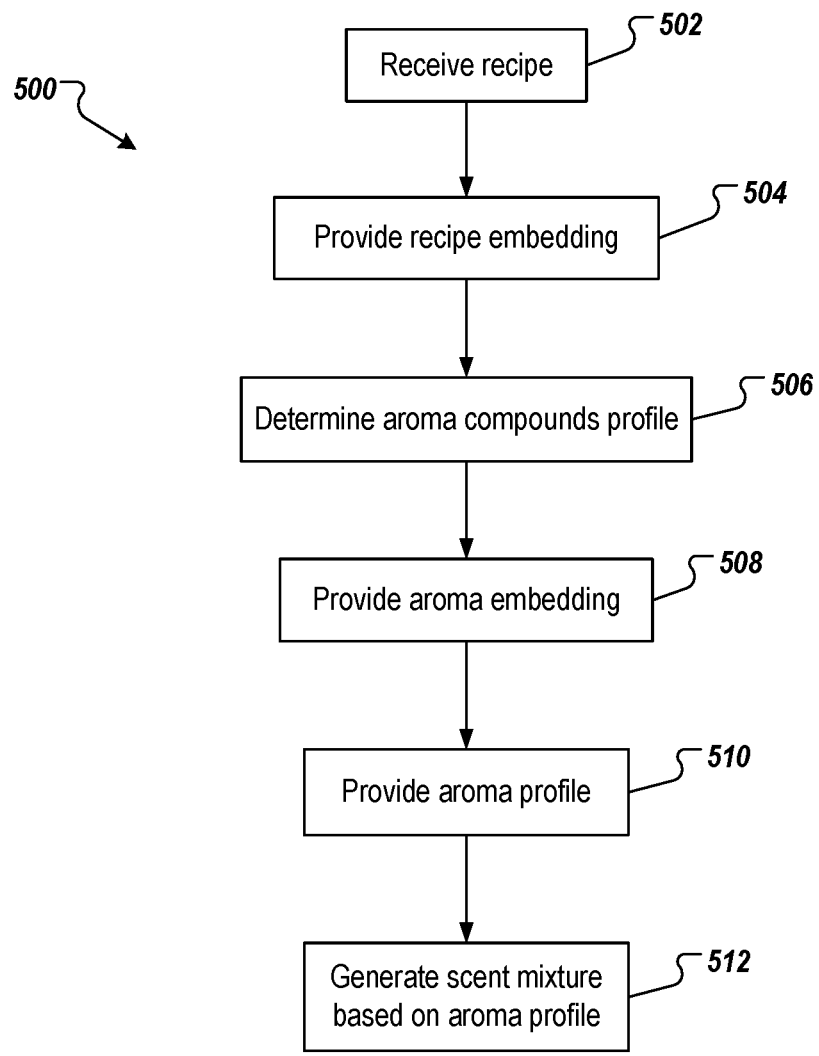
FIG. 5 depicts an example process that can be executed in accordance with implementations of the present disclosure.

FIG. 5 depicts an example process 500 that can be executed in accordance with implementations of the present disclosure. In some examples, the example process 500 is provided using one or more computer-executable programs executed by one or more computing devices.

A recipe is received (502). For example, and as described herein, the recipe 210 is received by the aromatic simulation platform 202 as a computer-readable file. In some examples, the recipe 210 includes a set of ingredients and a set of instructions for making a consumable from the set of ingredients. A recipe embedding is provided (504). For example, and as described herein, the recipe 210 is processed through the first AI model 204 to provide the recipe embedding 330. In some examples, the recipe embedding 330 includes an ingredient embedding and an instruction embedding. The recipe embedding 330 is a vector presentation of the ingredients and instructions of the recipe 210.

An aroma compounds profile is determined (506). For example, and as described herein, a set of ingredients of the recipe 210 is processed to determine an aroma compounds profile. In some examples, the extraction module 203 can transmit a request to a service, the request including the list of ingredients. In some examples, the service maintains a database of ingredients and, for each ingredient, a set of aroma compounds representative of a scent of the respective ingredient. In some examples, in response to the request, the service returns, for each ingredient, a set of aroma compounds. In some examples, the set of aroma compounds includes, for each compound, a concentration. The extraction module 203 provides the aroma compounds profile, which includes a set of aroma compounds, and, for each aroma compound, a concentration (e.g., as depicted in the example of Table 1). An aroma embedding is provided (508). For example, and as described herein, the aroma compounds profile is processed through the second AI model 206 to provide the aroma embedding 332. The aroma embedding 332 is a vector representation of the aroma compounds representative of the recipe 210.

An aroma profile is provided (510). For example, and as described herein, the recipe embedding 330 and the aroma embedding 332 are processed through the third AI model 208 to provide the aroma profile 212. For example, and as described herein, the third AI model 208 can include a BiLSTM model and the aroma profile can be viewed as a prediction of respective scents and quantities thereof that represent an expected scent of a consumable represented by the recipe 210. A scent mixture is generated based on the aroma profile (512). For example, and as described herein, the aroma profile 212 is sent to the aroma diffuser 104, which includes a set of aroma cartridges, each aroma cartridge corresponding to a scent. The aroma diffuser 104 can process the aroma profile to determine a quantity to release from each aroma cartridge in the set of aroma cartridges. As a result, the aroma diffuser 104 can release a mix of scents from the set of aroma cartridges based on respective quantities.

Implementations of the present disclosure are described in further detail with reference to example consumable recipes and example use cases. It is contemplated, however, that implementations of the present disclosure can be realized in any appropriate consumable recipe and/or any appropriate use case.

A first example use case includes interactive virtual simulation in the retail industry. In the retail industry, the aromatic simulation platform of the present disclosure enables customers to have a wider and more immersive testing experience of consumables, such as, within a store, restaurant, or coffee shop, for example, before purchasing a consumable. For example, the consumer can experience a recipe and, if satisfied, may make a purchase based on the recipe. If unsatisfied, the recipe can be modified, a modified aroma profile can be time- and resource-efficiently generated for the modified recipe, and the consumer can virtually experience the modified recipe. In some examples, the consumable can be a food, a drink, blended essential oils, fragrance, or the like. The customer can also customize the consumable (e.g., have some adjustment from the existing consumable) from the sensory experience before purchasing.

A second example use case includes similar consumable recommendations. The aroma profile corresponding to a consumable recipe generated by the aromatic simulation platform of the present disclosure can also be used to categorize and similar aroma profiles can be tagged with the same label, such as flavors like fruity, floral or woody. The customer is able to find out if there are other choices under the same label.

A third example use case includes cartridge optimization. As discussed above, the aroma diffuser is equipped with a limited number of aroma cartridges and the aroma diffuser may be expected to simulate the aroma experience of the consumable recipe based on these limited number of scents. Using implementations of the present disclosure, an operator of the virtual sensory experience is able to find out the most commonly used scents for simulating consumables. The operator can keep those scents on-hand and/or in the aroma diffuser without changing the aroma cartridges for another consumable recipe frequently.

Implementations and all of the functional operations described in this specification may be realized in digital electronic circuitry, or in computer software, firmware, or hardware, including the structures disclosed in this specification and their structural equivalents, or in combinations of one or more of them. Implementations may be realized as one or more computer program products (i.e., one or more modules of computer program instructions) encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question (e.g., code) that constitutes processor firmware, a protocol stack, a database management system, an operating system, or a combination of one or more of them. A propagated signal is an artificially generated signal (e.g., a machine-generated electrical, optical, or electromagnetic signal) that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry (e.g., an FPGA (field programmable gate array) or an ASIC (application specific integrated circuit)).

Processors suitable for the execution of a computer program include, by way of example, both general and special purpose microprocessors, and any one or more processors of any appropriate kind of digital computer. Generally, a processor will receive instructions and data from a read only memory or a random-access memory or both. Elements of a computer can include a processor for performing instructions and one or more memory devices for storing instructions and data. Generally, a computer will also include, or be operatively coupled to receive data from or transfer data to, or both, one or more mass storage devices for storing data (e.g., magnetic, magneto optical disks, or optical disks). However, a computer need not have such devices. Moreover, a computer may be embedded in another device (e.g., a mobile telephone, a personal digital assistant (PDA), a mobile audio player, a Global Positioning System (GPS) receiver). Computer readable media suitable for storing computer program instructions and data include all forms of non-volatile memory, media and memory devices, including by way of example semiconductor memory devices (e.g., EPROM, EEPROM, and flash memory devices); magnetic disks (e.g., internal hard disks or removable disks); magneto optical disks; and CD ROM and DVD-ROM disks. The processor and the memory may be supplemented by, or incorporated in, special purpose logic circuitry.

To provide for interaction with a user, implementations may be realized on a computer having a display device (e.g., a CRT (cathode ray tube), LCD (liquid crystal display), LED (light-emitting diode) monitor, for displaying information to the user and a keyboard and a pointing device (e.g., a mouse or a trackball), by which the user may provide input to the computer. Other kinds of devices may be used to provide for interaction with a user as well; for example, feedback provided to the user may be any appropriate form of sensory feedback (e.g., visual feedback, auditory feedback, or tactile feedback); and input from the user may be received in any appropriate form, including acoustic, speech, or tactile input.

Implementations may be realized in a computing system that includes a back end component (e.g., as a data server), or that includes a middleware component (e.g., an application server), or that includes a front end component (e.g., a client computer having a graphical user interface or a Web browser through which a user may interact with an implementation), or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN") (e.g., the Internet).

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the disclosure or of what may be claimed, but rather as descriptions of features specific to particular implementations. Certain features that are described in this specification in the context of separate implementations may also be implemented in combination in a single implementation. Conversely, various features that are described in the context of a single implementation may also be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products.

A number of implementations have been described. Nevertheless, it will be understood that various modifications may be made without departing from the spirit and scope of the disclosure. For example, various forms of the flows shown above may be used, with steps re-ordered, added, or removed. Accordingly, other implementations are within the scope of the following claims.

What is claimed is:

1. A computer-implemented method for releasing multiple scents from an aroma diffuser using sensory profile prediction by an aromatic simulation platform, the computer-implemented method comprising:
   receiving, by the aromatic simulation platform, a recipe comprising descriptions indicative of ingredients of a consumable;
   processing the recipe through a first neural network to provide a recipe embedding;
   processing an ingredients profile to determine an aroma compounds profile representing the ingredients of the ingredients profile, the aroma compounds profile representing a set of aroma compounds for each ingredient in the ingredients profile and, for each aroma compound, a concentration;
   processing the aroma compounds profile through a second neural network to provide an aroma embedding;
   processing the recipe embedding and the aroma embedding through a third neural network to provide an aroma profile representative of the consumable of the recipe;
   processing, by an aroma diffuser, the aroma profile to determine a quantity to release from each aroma cartridge in a set of aroma cartridges, each aroma cartridge corresponding to a scent; and
   releasing, by the aroma diffuser, a mix of scents from the set of aroma cartridges based on respective quantities.

2. The computer-implemented method of claim 1, wherein the scent corresponds to part of the aroma compounds, and the aroma profile is indicative of proportion of each scent in the mix of scents.

3. The computer-implemented method of claim 1, wherein the recipe is a new recipe or a modified recipe with changes in comparison with one of the recipes stored in a database.

4. The computer-implemented method of claim 1, further comprising:
   extracting, by the first neural network, ingredient vocabularies from descriptions representative of the ingredients in the recipe;
   encoding, by the first neural network, the ingredient vocabularies to provide an ingredient embedding;
   extracting, by the first neural network, instruction vocabularies from descriptions representative of instructions in the recipe;
   encoding, by the first neural network, the instruction vocabularies to provide an instruction embedding; and
   combing the ingredient embedding and the instruction embedding to provide the recipe embedding.

5. The computer-implemented method of claim 1, further comprising:
   deriving, by the second neural network, molecular embedding vectors corresponding to each aroma compound;
   extracting, by the second neural network, quantities of each of the aroma compounds from the recipe to derive weights of each aroma compound;
   processing, by the second neural network, to mix the molecular embedding vectors and the weight corresponding to the same aroma compound to derive a set of weight-mixed molecular embedding vectors; and
   deriving, by the second neural network, the aroma embedding based on the weight-mixed molecular embedding vectors.

6. The computer-implemented method of claim 1, wherein the third neural network comprising a bi-directional long short-term memory (BiLSTM) model.

7. Non-transitory computer-readable storage media coupled to one or more processors and having instructions stored thereon which, when executed by the one or more processors, cause the one or more processors to perform operations for releasing multiple scents from an aroma diffuser using sensory profile prediction by an aromatic simulation platform, the operations comprising:
   receiving, by the aromatic simulation platform, a recipe comprising descriptions indicative of ingredients of a consumable;
   processing the recipe through a first neural network to provide a recipe embedding;
   processing an ingredients profile to determine an aroma compounds profile representing the ingredients of the ingredients profile, the aroma compounds profile representing a set of aroma compounds for each ingredient in the ingredients profile and, for each aroma compound, a concentration;
   processing the aroma compounds profile through a second neural network to provide an aroma embedding;
   processing the recipe embedding and the aroma embedding through a third neural network to provide an aroma profile representative of the consumable of the recipe;
   processing, by an aroma diffuser, the aroma profile to determine a quantity to release from each aroma cartridge in a set of aroma cartridges, each aroma cartridge corresponding to a scent; and
   releasing, by the aroma diffuser, a mix of scents from the set of aroma cartridges based on respective quantities.

8. The non-transitory computer-readable storage media of claim 7, wherein the scent corresponds to part of the aroma compounds, and the aroma profile is indicative of proportion of each scent in the mix of scents.

9. The non-transitory computer-readable storage media of claim 7, the recipe is a new recipe or a modified recipe with changes in comparison with one of the recipes stored in a database.

10. The non-transitory computer-readable storage media of claim 7, wherein operations further comprise:

extracting, by the first neural network, ingredient vocabularies from descriptions representative of the ingredients in the recipe;

encoding, by the first neural network, the ingredient vocabularies to provide an ingredient embedding;

extracting, by the first neural network, instruction vocabularies from descriptions representative of instructions in the recipe;

encoding, by the first neural network, the instruction vocabularies to provide an instruction embedding; and combing the ingredient embedding and the instruction embedding to provide the recipe embedding.

11. The non-transitory computer-readable storage media of claim 7, wherein operations further comprise:

deriving, by the second neural network, molecular embedding vectors corresponding to each aroma compound;

extracting, by the second neural network, quantities of each of the aroma compounds from the recipe to derive weights of each aroma compound;

processing, by the second neural network, to mix the molecular embedding vectors and the weight corresponding to the same aroma compound to derive a set of weight-mixed molecular embedding vectors; and deriving, by the second neural network, the aroma embedding based on the weight-mixed molecular embedding vectors.

12. The non-transitory computer-readable storage media of claim 7, wherein the third neural network comprising a bi-directional long short-term memory (BiLSTM) model.

13. A system, comprising:

an aroma diffuser that is configured to release one or more scents; and non-transitory computer-readable storage media coupled to the computing device and having instructions stored thereon which, when executed by one or more computing devices, cause the one or more computing devices to perform operations for releasing multiple scents from the aroma diffuser using sensory profile prediction by an aromatic simulation platform, the operations comprising:

receiving, by the aromatic simulation platform, a recipe comprising descriptions indicative of ingredients of a consumable;

processing the recipe through a first neural network to provide a recipe embedding;

processing an ingredients profile to determine an aroma compounds profile representing the ingredients of the ingredients profile, the aroma compounds profile representing a set of aroma compounds for each ingredient in the ingredients profile and, for each aroma compound, a concentration;

processing the aroma compounds profile through a second neural network to provide an aroma embedding;

processing the recipe embedding and the aroma embedding through a third neural network to provide an aroma profile representative of the consumable of the recipe;

processing, by an aroma diffuser, the aroma profile to determine a quantity to release from each aroma cartridge in a set of aroma cartridges, each aroma cartridge corresponding to a scent; and releasing, by the aroma diffuser, a mix of scents from the set of aroma cartridges based on respective quantities.

14. The system of claim 13, wherein the scent corresponds to part of the aroma compounds, and the aroma profile is indicative of proportion of each scent in the mix of scents.

15. The system of claim 13, wherein the recipe is a new recipe or a modified recipe with changes in comparison with one of the recipes stored in a database.

16. The system of claim 13, wherein operations further comprise:

extracting, by the first neural network, ingredient vocabularies from descriptions representative of the ingredients in the recipe;

encoding, by the first neural network, the ingredient vocabularies to provide an ingredient embedding;

extracting, by the first neural network, instruction vocabularies from descriptions representative of instructions in the recipe;

encoding, by the first neural network, the instruction vocabularies to provide an instruction embedding; and combing the ingredient embedding and the instruction embedding to provide the recipe embedding.

17. The system of claim 13, wherein operations further comprise:

deriving, by the second neural network, molecular embedding vectors corresponding to each aroma compound;

extracting, by the second neural network, quantities of each of the aroma compounds from the recipe to derive weights of each aroma compound;

processing, by the second neural network, to mix the molecular embedding vectors and the weight corresponding to the same aroma compound to derive a set of weight-mixed molecular embedding vectors; and deriving, by the second neural network, the aroma embedding based on the weight-mixed molecular embedding vectors.

* * * * *